US008864677B2

(12) United States Patent
Li et al.

(10) Patent No.: US 8,864,677 B2
(45) Date of Patent: Oct. 21, 2014

(54) SYSTEMS AND METHODS FOR MYOCARDIAL ISCHEMIA DETECTION

(75) Inventors: Dan Li, Shoreview, MN (US); Haresh G. Sachanandani, Los Angeles, CA (US); Michael John Kane, Clonmel (IE); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1172 days.

(21) Appl. No.: 12/402,224

(22) Filed: Mar. 11, 2009

(65) Prior Publication Data

US 2009/0234211 A1 Sep. 17, 2009

Related U.S. Application Data

(60) Provisional application No. 61/036,243, filed on Mar. 13, 2008.

(51) Int. Cl.
*A61B 5/02* (2006.01)
*A61B 5/04* (2006.01)
*A61B 5/145* (2006.01)
*A61N 1/362* (2006.01)
*A61B 5/0468* (2006.01)
*A61N 1/365* (2006.01)
*A61B 5/1459* (2006.01)
*A61B 5/0402* (2006.01)

(52) U.S. Cl.
CPC ........... *A61B 5/0402* (2013.01); *A61B 5/14546* (2013.01); *A61B 5/14532* (2013.01); *A61N 1/3627* (2013.01); *A61B 5/0468* (2013.01); *A61N 1/36585* (2013.01); *A61B 5/1459* (2013.01)
USPC ........................................ 600/483; 600/513

(58) Field of Classification Search
USPC .................................. 600/345, 347, 483, 513
See application file for complete search history.

(56) References Cited

U.S. PATENT DOCUMENTS 4,860,751 A * 8/1989 Callaghan ........................ 607/16
4,924,875 A * 5/1990 Chamoun ...................... 600/509
5,313,953 A * 5/1994 Yomtov et al. ................ 600/508

(Continued)

OTHER PUBLICATIONS

Adams-Hamoda, Mary G. et al., "Factors to Consider When Analyzing 12-Lead Electrocardiograms for Evidence of Acute Myocardial Ischemia", *American Journal of Critical Care* Jan. 2003 , vol. 12, No. 1.

(Continued)

*Primary Examiner* — Navin Natnithithadha
*Assistant Examiner* — Michael R Bloch
(74) *Attorney, Agent, or Firm* — Pauly, Devries Smith & Deffner, LLC

(57) ABSTRACT

Embodiments of the invention are related to devices and methods for myocardial ischemia detection, amongst other things. In an embodiment, the invention includes an implantable medical device including control circuitry, an electrical field sensor in communication with the control circuitry, the electrical field sensor configured to generate a signal corresponding to cardiac electrical fields. The implantable medical device can also include a chemical sensor in communication with the control circuitry, the chemical sensor configured to generate a signal corresponding to the concentration of a physiological analyte that affects cardiac electrical field waveform morphology. The control circuitry can be configured to monitor for the presence of myocardial ischemia by evaluating both the signal generated by the electrical field sensor and the signal generated by the chemical sensor. Other embodiments are also included herein.

14 Claims, 9 Drawing Sheets

(56) References Cited

U.S. PATENT DOCUMENTS

| | | | |
|---|---|---|---|
| 5,634,468 A * | 6/1997 | Platt et al. | 600/509 |
| 6,430,435 B1 | 8/2002 | Hsu et al. | |
| 6,660,526 B2 | 12/2003 | Benco et al. | |
| 7,006,858 B2 | 2/2006 | Silver et al. | |
| 7,016,730 B2 * | 3/2006 | Ternes | 607/17 |
| 7,031,764 B2 | 4/2006 | Schwartz et al. | |
| 7,181,261 B2 | 2/2007 | Silver et al. | |
| 7,894,884 B2 * | 2/2011 | Song et al. | 600/509 |
| 2006/0116593 A1 | 6/2006 | Zhang et al. | |
| 2006/0167365 A1 | 7/2006 | Bharmi | |
| 2006/0167518 A1 | 7/2006 | Gill et al. | |
| 2006/0241709 A1 | 10/2006 | Soykan et al. | |
| 2007/0179357 A1* | 8/2007 | Bardy | 600/300 |
| 2007/0270675 A1 | 11/2007 | Kane et al. | |
| 2008/0046038 A1* | 2/2008 | Hill et al. | 607/60 |
| 2008/0177194 A1 | 7/2008 | Zhang et al. | |
| 2009/0099468 A1* | 4/2009 | Thiagalingam et al. | 600/515 |

OTHER PUBLICATIONS

Paavonen, K. J. et al., "Response of the QT interval to mental and physical stress in types LQT1 and LQT2 of the long QT syndrome", *Heart Journal* 2001, Issue 86, pp. 39-44.

Parham, Walter A. et al., "Hyperkalemia Revisited", *Texas Heart Institute Journal* 2006, issue33: pp. 40-47.

Vogt, S. et al., "Efficacy of ion-selective probes in early epicardial in vivo detection of myocardial ischemia", *Physiological Measurement* Dec. 2004, Issue 6: 25 N21-N26.

Voht, S et al., "Detection of myocardial ischemia by epicardial detection of potassium ion activity", *Biobed Tech* (*Berl*) Nov. 2002, 47(11) : pp. 294-301 (Abstract only).

Wang, Kyuhyun et al., "ST-Segment Elevation in Conditions Other Than Acute Myocardial Infarction", *The New England Journal of Medicine* 2003, Issue 349; pp. 2128-2135.

* cited by examiner

SYSTEMS AND METHODS FOR MYOCARDIAL ISCHEMIA DETECTION

RELATED APPLICATIONS

This application claims priority to provisional U.S. patent application 61/036,243, filed Mar. 13, 2008, the contents of which are herein incorporated by reference.

TECHNICAL FIELD

This disclosure relates generally to medical devices and, more particularly, to medical devices capable of detecting myocardial ischemia and related methods, amongst other things.

BACKGROUND OF THE INVENTION

Myocardial ischemia is a common condition with life-threatening consequences. Myocardial ischemia occurs when blood flow to the heart muscle (myocardium) is obstructed by a partial or complete blockage of a coronary artery. Severe myocardial ischemia may lead to myocardial infarction. Myocardial ischemia may also cause a serious abnormal heart rhythm (arrhythmia), which can cause fainting or even sudden death. The prevalence of ischemic heart disease is estimated to be approximately 6.40% in the U.S. population.

Because of the high prevalence of ischemic heart disease and the very serious nature of its possible effects, monitoring and quick diagnosis of myocardial ischemia are of great importance to clinicians. This is particularly true of patients with implantable cardiac rhythm management (CRM) devices because the prevalence of ischemic heart disease is relatively high in the population of patients with such devices.

Electrocardiography is an important tool for the monitoring and diagnosis of various cardiac conditions. Extracellular cardiac electrical fields are generated by ion fluxes across cell membranes and between adjacent cells. These ion currents are synchronized by cardiac activation and recovery sequences to generate a cardiac electrical field in and around the heart that varies with time during cardiac cycles. The process of measuring these time varying cardiac electrical fields is known as electrocardiography. Electrocardiography represents a widely used clinical tool for the detection and diagnosis of a broad range of cardiac conditions.

Acute myocardial ischemia can be observed using electrocardiography. Severe acute ischemia can reduce the resting membrane potential, shorten the duration of the action potential in the ischemic area, and decrease the rate of rise and amplitude of phase 0 of the action potential (when voltage-gated sodium channels open). These changes cause a voltage gradient between normal and ischemic zones that lead to current flow between these regions, represented on an electrocardiogram (ECG) by deviation of the ST segment. As such, an acute ischemic condition, such as acute myocardial infarction, is recognized by electrocardiography through ST-segment elevation.

SUMMARY OF THE INVENTION

Embodiments of the invention are related to medical devices capable of detecting myocardial ischemia and related methods, amongst other things. In an embodiment, the invention includes using cardiac electrogram signals and chemical sensor signals to identify and differentiate myocardial ischemia from conditions characterized by abnormal analyte concentrations. The electrogram signals can be gathered via an electrical sensor that, in some embodiments, is part of an implanted medical device. A chemical sensor can also be included in the implanted medical device. In some embodiments, when cardiac electrogram data are gathered that are consistent with myocardial ischemia, the chemical sensor can be activated to determine whether the cardiac electrogram is truly a result of myocardial ischemia or simply a result of abnormal analyte levels. In some embodiments, the cardiac electrogram can be compared with known cardiac electrogram morphological templates that are stored in a database, to identify whether the cardiac electrogram is a result of myocardial ischemia or abnormal analyte (or chemical) levels.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

It can be difficult to correctly identify a patient who is suffering from acute myocardial ischemia on the basis of electrocardiography alone. This is because other conditions can mimic some of the typical electrocardiographic changes associated with acute myocardial ischemia. By way of example, ST segment elevation can result from hyperkalemia (the presence of a higher than normal physiological concentration of potassium). Thus it can be difficult to distinguish between a patient who is suffering from a life-threatening ischemic condition and one who has abnormal levels of potassium, particularly for those with implantable medical devices that have a limited numbers of cardiac vectors for electrocardiography.

However, in various embodiments included herein, electrocardiography findings are combined with other data points to enable more accurate detection of myocardial ischemia. By way of example, various embodiments herein include sensing physiological chemical concentrations, such as potassium ion concentrations, in conjunction with electrocardiography in order to accurately detect myocardial ischemia. Embodiments of the invention can specifically include an implantable medical device including a chemical sensor, such as a potassium sensor, and an electrical field sensor. The implantable medical device can be configured to use both electrocardiography data and chemical sensor data in identifying myocardial ischemia. Various aspects of exemplary medical devices that can include such ischemia detection features will now be described in greater detail.

Figure 1:
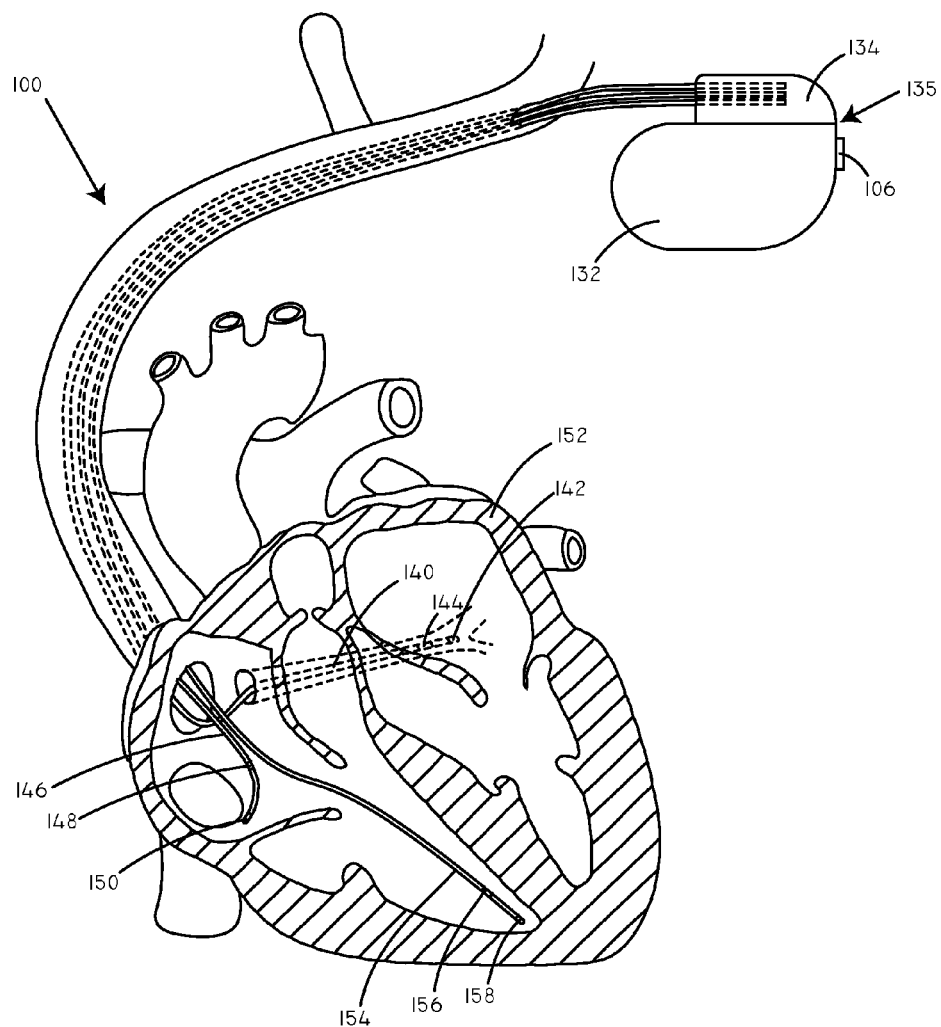
FIG. 1 is a schematic view of an implantable medical system.

Referring now to FIG. 1, a schematic view is shown of an implantable medical system 100. The implantable medical system 100 includes an implantable medical device 135 and one or more stimulation leads 140, 146, and 154. In various embodiments, the implantable medical device 135 can include a cardiac rhythm management device, such as a pacemaker, a cardiac resynchronization therapy (CRT) device, a remodeling control therapy (RCT) device, a cardioverter/defibrillator, or a pacemaker-cardioverter/defibrillator. In some embodiments, the implantable medical device 135 can include a neurological stimulation device.

The implantable medical device 135 can include a pulse generator housing 132 and a header 134. The term "pulse generator housing" as used herein shall refer to the part or parts of an implanted medical device, such as a cardiac rhythm management device or a neurological therapy device, containing the power source and circuitry for delivering pacing therapy, electrical stimulation, and/or shock therapy. Together, the pulse generator housing 132, the contents therein, and the header 134 can be referred to as a pulse generator. It will be appreciated that embodiments of the invention can also be used in conjunction with implantable medical devices that may lack pulse generators such as monitoring devices and drug delivery devices.

In FIG. 1, the proximal ends of the stimulation leads 140, 146, and 154 are disposed within the header 134. The stimulation leads 140, 146, and 154 transvenously pass to the heart 152. In this view, stimulation lead 140 passes into the coronary venous system, stimulation lead 150 passes into the right atrium, and stimulation lead 154 passes into the right ventricle. However, it will be appreciated that stimulation leads can be disposed in various places within or around the heart. Stimulation lead 140 includes a tip electrode 142 and a ring electrode 144. Stimulation leads 146 and 154 also include tip electrodes 150 and 158 and ring electrodes 148 and 156, respectively. It will be appreciated that stimulation leads can include different numbers of electrodes. For example, in some embodiments, a stimulation lead may only include a single electrode. Depending on the configuration, the stimulation leads can provide electrical and/or optical communication between the distal ends of the stimulation leads and the pulse generator. In operation, the pulse generator may generate pacing pulses or therapeutic shocks which are delivered to the heart 152 via the electrodes of the stimulation leads. In many embodiments, the stimulation leads include a material that is electrically conductive in order to deliver the pacing pulses or therapeutic shocks.

Figure 2:
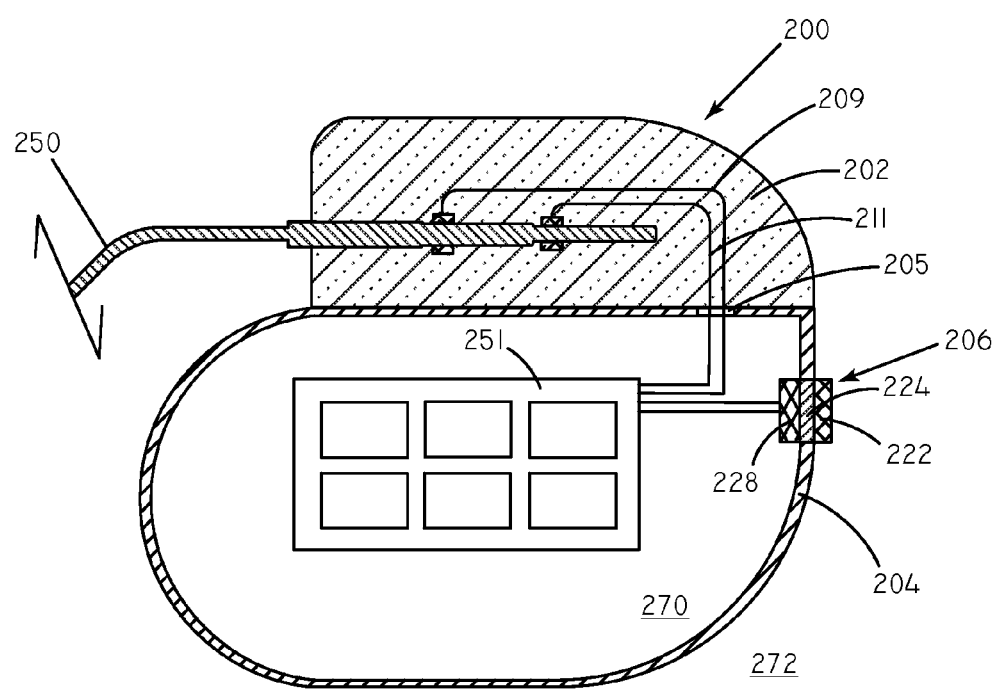
FIG. 2 is a schematic cross-sectional view of an implantable medical device in accordance with an embodiment of the invention.

The implantable medical system 100 can also be configured to sense electrical activity of the heart. By way of example, the implantable medical system 100 can include an electrical field sensor (such as shown in FIG. 2 as part of control circuitry 251). Specifically, the implantable medical system 100 can use one or more electrodes, such as the electrodes on the stimulation leads 142, 144, 148, 150, 156, and/or 158, in order to sense electrical activity of the heart, such as a time-varying electrical potential. In some embodiments, the pulse generator housing 132 can serve as an electrode for purposes of sensing electrical activity and/or delivering electrical stimulation.

The implantable medical system 100 can also include a chemical sensor 106. The chemical sensor 106 can be configured to measure the concentration of physiological analytes. For example, in some embodiments, the chemical sensor can be configured to measure the physiological concentrations of potassium. Further examples of chemical analytes that can be measured are described in greater detail below.

Referring now to FIG. 2, a schematic cross-sectional view of an implantable medical device 200 is shown in accordance with an embodiment of the invention. The implantable medical device 200 includes a header assembly 202 and a housing 204. The housing 204 of the implantable medical device 200 can include various materials such as metals, polymers, ceramics, and the like. In one embodiment, the housing 204 is formed of titanium. The header assembly 202 can be coupled to one or more electrical stimulation leads 250. The header assembly 202 serves to provide fixation of the proximal end of one or more leads and electrically couples the leads to components within the housing 204. The header assembly 202 can be formed of various materials including metals, polymers, ceramics, and the like.

The housing 204 defines an interior volume 270 that is hermetically sealed off from the volume 272 outside of the device 200. Various electrical conductors 209, 211 can pass from the header 202 through a feed-through structure 205, and into the interior volume 270. As such, the conductors 209, 211 can serve to provide electrical communication between the electrical stimulation lead 250 and control circuitry 251 disposed within the interior volume 270 of the housing 204. The control circuitry 251 can include various components such as a microprocessor, memory (such as random access memory (RAM) and/or read only memory (ROM)), a telemetry module, electrical field sensor and stimulation circuitry, a power supply (such as a battery), and an optical sensor interface channel, amongst others.

The implantable medical device 200 can incorporate, for example, an electrical field sensor that is configured to generate a signal corresponding to cardiac electric fields. The electrical field sensor can include a first electrode and a second electrode. The electrodes of the electrical field sensor can be the same electrodes used to provide electrical stimulation or can be different electrodes. In some embodiments, one or more electrodes can be mounted on one or more electrical stimulation leads 250. In some embodiments, the housing 204 can serve as an electrode. The electrodes can be in communication with the electrical field sensor and stimulation circuitry. The electrical field sensor can include a circuit in order to measure the electrical potential difference (voltage) between the first electrode and the second electrode.

The implantable medical device 200 can also include a chemical sensor 206. In the embodiment shown in FIG. 2, the chemical sensor is an optical chemical sensor. However, in other embodiments the chemical sensor can be a potentiometric chemical sensor. The chemical sensor 206 can specifically include a chemical sensing element 222, an optical window 224, and an electro-optical module 228. The electro-optical module 228 can be disposed within the hermetically sealed interior volume 270 of the housing 204. The electro-optical module 228 can be in electrical communication with the circuitry 251 within the interior volume 270, and in some embodiments, the control circuitry 251 is configured to selectively activate the chemical sensor. The chemical sensor 206 can also be configured to be chronically implanted.

The chemical sensor 206 can include an electro-optical module 228 coupled to the optical window 224. The electro-optical module 228 can specifically include one or more optical excitation assemblies. Each optical excitation assembly can include various light sources such as light-emitting diodes (LEDs), vertical-cavity surface-emitting lasers (VCSELs), electroluminescent (EL) devices or the like. The electro-optical module 228 can also include one or more optical detection assemblies (not shown). Each optical detection assembly can include one or more photodiodes, avalanche photodiodes, a photodiode array, a photo transistor, a multi-element photo sensor, a complementary metal oxide semiconductor (CMOS) photo sensor, or the like.

The chemical sensing element 222 can be disposed on the optical window 224. The chemical sensing element 222 can be configured to detect a physiological analyte by exhibiting an optically detectable response to the physiological analyte. The physiological analyte can be, for example, calcium, potassium, or glucose, for example. In operation, analytes of interest from the in vivo environment can diffuse into the chemical sensing element 222 causing a detectable change in the optical properties of the chemical sensing element 222. Light can be generated by the electro-optical module 228 and can pass through the optical window 224 and into the chemical sensing element 222. Light can then either be preferentially reflected from or re-emitted by the chemical sensing element 222 proportional to the sensed analyte and pass back through the optical window 224 before being received by the electro-optical module 228. Various aspects of exemplary chemical sensors are described in greater detail in U.S. Pub. App. No. 2007/0270675, the content of which is herein incorporated by reference in its entirety.

In some embodiments, the chemical sensor can be part of an external non-implantable device. By way of example, the chemical sensor can be part of an external testing system that can be used by the patient or a clinician. In some embodiments, data regarding the analyte of interest can then be transmitted from the external chemical sensor through wired or wireless techniques for further processing.

Figure 3:
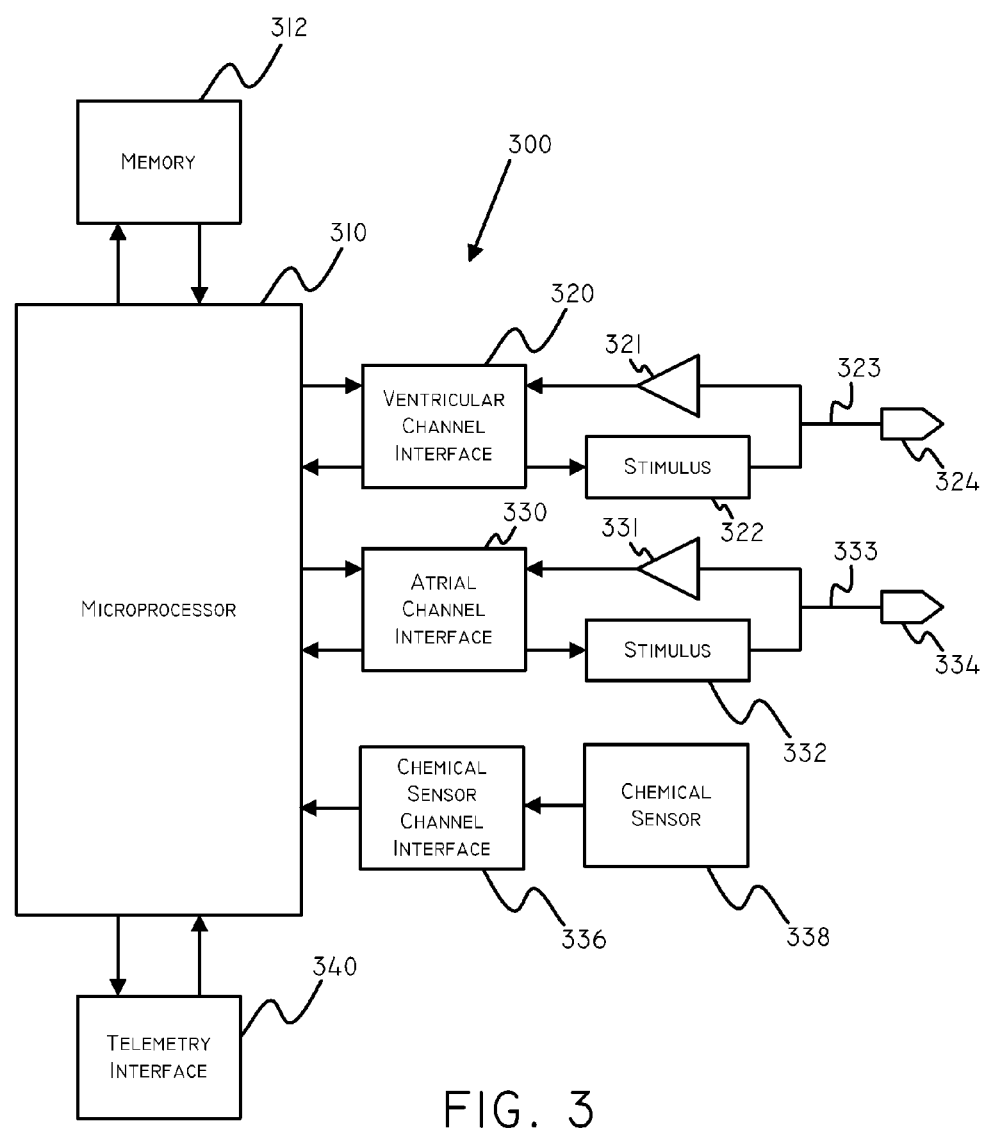
FIG. 3 is a schematic diagram of components of an implantable medical device in accordance with an embodiment of the invention.

Elements of some embodiments of an implantable medical device are shown in FIG. 3. However, it will be appreciated that some embodiments can include additional elements beyond those shown in FIG. 3. In addition, some embodiments may lack some elements shown in FIG. 3. The medical device 300 can sense cardiac events through one or more sensing channels and outputs pacing pulses to the heart via one or more pacing channels in accordance with a programmed pacing mode. A microprocessor 310 communicates with a memory 312 via a bidirectional data bus. The memory 312 typically comprises read only memory (ROM) or random access memory (RAM) for program storage and RAM for data storage.

The implantable medical device has atrial sensing and pacing channels comprising at least a first electrode 334, lead 333, sensing amplifier 331, output circuit 332, and an atrial channel interface 330 which communicates bidirectionally with a port of microprocessor 310. In this embodiment, the device also has ventricular sensing and pacing channels comprising at least a second electrode 324, lead 323, sensing amplifier 321, output circuit 322, and ventricular channel interface 320. For each channel, the same lead and electrode are used for both sensing and pacing. The channel interfaces 320 and 330 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device can also include a chemical sensor 338 and a chemical sensor channel interface 336. A telemetry interface 340 is also provided for communicating with an external programmer.

Figure 4:
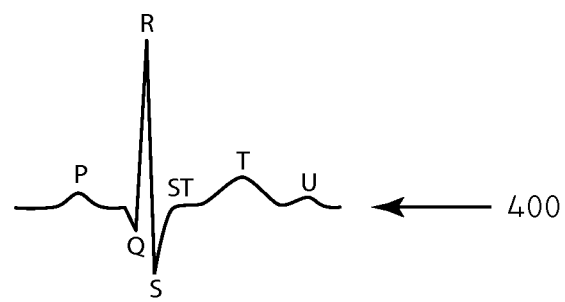
FIG. 4 is a chart illustrating an exemplary normal cardiac electrogram.

In various embodiments herein, devices and system such as those illustrated in FIGS. 1-3 can be configured to evaluate and/or characterize the morphology of a cardiac electrogram as part of a process for identifying myocardial ischemia. FIG. 4 is a view of an exemplary cardiac electrogram 400, representative of the morphology that would be observed in at least a portion of healthy adults. As can be seen, the electrogram graph includes a P wave reflecting atrial contraction, a QRS segment reflecting ventricular contraction, an ST segment, a T wave corresponding to rapid ventricular repolarization, and a U wave. It will be appreciated that this is an idealized representation of an electrogram and in practice actual electrogram recordings may appear somewhat different based on factors such as the location of electrodes, individual patient characteristics, etc. Specifically, the exemplary electrogram of FIG. 4 is similar in appearance to what would be expected from an electrocardiogram (ECG) taken with a device outside of the body, however, it will be appreciated that this is provided for purposes of clarity of illustration, and that electrograms as taken with implantable devices are included within the scope of embodiments herein.

Figure 5:
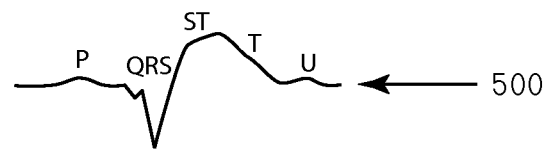
FIG. 5 is a chart illustrating ST segment elevation in a cardiac electrogram.

The morphology of a cardiac electrogram can change significantly in response to conditions such as myocardial ischemia and hyperkalemia. Illustrating this point, FIG. 5 is an additional view of an exemplary cardiac electrogram 500 representative of individuals with a condition such as myocardial ischemia and/or hyperkalemia. In the electrogram graph of FIG. 5, the ST-segment is elevated. ST segment elevation can be the result of a number of health concerns such as, for example, myocardial ischemia, chemical imbalance such as hypokalemia or hyperkalemia, or abnormal blood glucose levels.

In various embodiments herein, causes of electrogram abnormalities, such as ST segment elevation illustrated in FIG. 5, other than myocardial ischemia can be ruled out by analyzing additional data. For example, if the cardiac electrogram reflects data consistent with both chemical imbalance and myocardial ischemia, then the result can be narrowed by using a chemical sensor to determine chemical levels. If chemical levels are normal, then the abnormal cardiac electrogram is more likely to be a result of myocardial ischemia. However, if chemical levels are abnormal, then an abnormal cardiac electrogram is less likely to be a result of myocardial ischemia.

As such, in some embodiments, control circuitry, which can be internal to an implantable medical device, can be configured to confirm the accuracy of myocardial ischemia identification by the electrical field sensor (and, therefore, the ST/T morphology) based on the signal generated by the chemical sensor. In some embodiments the system can be configured to generate an alert when myocardial ischemia is deemed present based on evaluating both the signal generated by the electrical field sensor and the signal generated by the chemical sensor. The alert can be an audio alert, an electronic message, and/or another type of signal.

Figure 6:
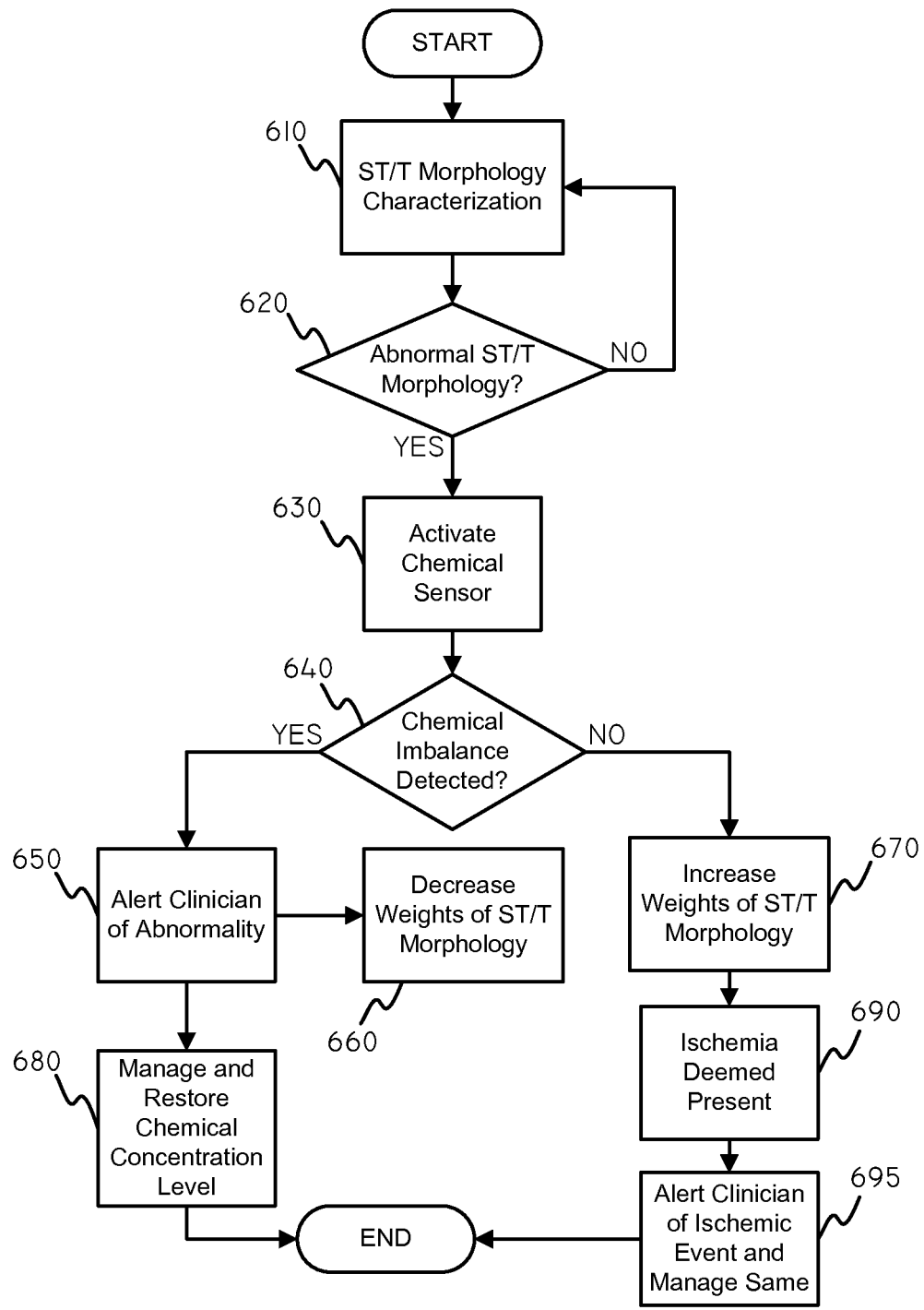
FIG. 6 is a flow chart in accordance with at least one embodiment of the invention.

FIG. 6 is a flow diagram illustrating a method in accordance with at least one embodiment of the invention. In one operation, the ST/T morphology is characterized 610. The ST/T morphology is essentially data associated with a portion of cardiac electrogram data, which is based on signals provided by an electrical field sensor.

In another operation, the system can determine whether or not the ST/T morphology is abnormal 620. The ST/T morphology is determined to be abnormal for purposes of the technology disclosed herein if the ST/T morphology deviates from that which is known to substantially represent a normal, healthy cardiac rhythm. In some embodiments, ST/T morphology can be determined to be abnormal for purposes of the technology disclosed herein if the ST/T morphology is consistent with that which is known to substantially represent a cardiac rhythm resulting from myocardial ischemia, chemical imbalance, or the like. In some embodiments, ST/T morphology is deemed to be abnormal if the ST/T segment is elevated. In some embodiments, ST/T morphology is deemed to be abnormal if the observed ST/T morphology differs from a "normal" morphology template. Aspects of cardiac electrogram morphological processing are described in U.S. Pat. Nos. 7,031,764, and 6,430,435, the contents of both of which are herein incorporated by reference in their entirety.

If the ST/T morphology is not abnormal, then the system can go back to morphology characterization. However, if the ST/T morphology is abnormal, a chemical sensor can be activated 630 in another operation. By way of example, a chemical sensor configured to detect concentrations of potassium ion can be activated. Activation may occur remotely from a computer terminal or processor, for example, or by internal control circuitry.

Data from the chemical sensor can be used to determine whether or not there is a chemical imbalance in another operation 640. A chemical imbalance is defined as a concentration of a particular chemical or various chemicals in the blood that deviates from a substantially normal or healthy range. Exemplary analytes that can be detected through a chemical sensor are potassium, calcium, and glucose, as examples. Normal serum potassium concentration is between about 3.8 to 5.0 mEq/L (milliequivalent per liter). In some embodiments, serum potassium concentration above 5.0 mEq/L is deemed to be hyperkalemia. In some embodiments, serum potassium concentration below 3.8 mEq/L is deemed to be hypokalemia. Normal serum calcium levels are between about 8.5 mg/dL to 10.2 mg/dL. In some embodiments, serum calcium levels above 10.2 mg/dL or below 8.5 mg/dL are deemed to be a chemical imbalance. Normal serum glucose levels are between 90 and 130 milligrams per deciliter (mg/dL). In some embodiment, serum glucose levels above 130 mg/dL or below 90 mg/dL are deemed to be a chemical imbalance.

Other analytes that can be detected by the chemical sensor can also include acetic acid (acetate), aconitic acid (aconitate), ammonium, blood urea nitrogen (BUN), B-type natriuretic peptide (BNP), bromate, carbon dioxide, cardiac specific troponin, chloride, choline, citric acid (citrate), cortisol, copper, creatinine, creatinine kinase, fluoride, formic acid (formate), hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, pyruvic acid (pyruvate), selenite, sodium, sulfate, sulfite, urea, uric acid, zinc, norephedrine, ephedrine, and various other compounds.

If a chemical imbalance is detected, a clinician can be alerted 650. For example, a notification can be send to the clinician. The notification can be sent electronically and displayed on a screen. In some embodiments, an audible alert can be generated. In some embodiments, therapy can be initiated 680 in order to manage and restore normal chemical levels. For example, the patient can be prompted to take electrolyte supplements. Optionally, drug therapy, such as diuretic therapy, can be adjusted in order to alleviate the chemical imbalance.

In some embodiments, where a chemical imbalance is detected the weight of the ST/T morphology as used in subsequent processes for detection of myocardial ischemia is decreased 660. By way of example, a value can be assigned to a weighting parameter such that when the system determines whether or not abnormal ST/T morphology is present (as in operation 620), the system is less likely to deem the ST/T morphology as being abnormal. In other words, less importance can be attributed to the ST/T morphology in an algorithm to detect myocardial ischemia. The decreased weighting can be implemented through manual data entry in a computer program, for example, or automatically. One way data can be entered in is through a programmer/recorder/monitor (PRM) device. Exemplary PRM devices include the Model 3120 Programmer, available from Boston Scientific Corporation, Natick, Mass. In general, a weighting parameter can be assigned a default value when the system is initially programmed. The value of the weight parameter can be changed from the default value according to the preferences of the clinician or through algorithms such as that shown in FIG. 6.

However, if no chemical imbalance is detected, then it is more likely that the abnormal ST/T morphology is actually a result of myocardial ischemia. In some embodiments, where no chemical imbalance is detected the weight of the ST/T morphology as used in subsequent processes for detection of myocardial ischemia is increased 670. By way of example, a value can be assigned to a weighting parameter such that when the system determines whether or not abnormal ST/T morphology is present (as in operation 620), the system is more likely to deem the ST/T morphology as being abnormal. The increased weighting can be implemented through manual data entry in a computer program or automatically.

If abnormal ST/T morphology is detected and if chemical analyte concentrations are within normal bounds, then ischemia can be deemed to be present by the system 690. Optionally, further steps 695 can be taken after ischemia is deemed to be present such as alerting a clinician, initiating appropriate therapy to manage the ischemia, and the like.

Figure 7:
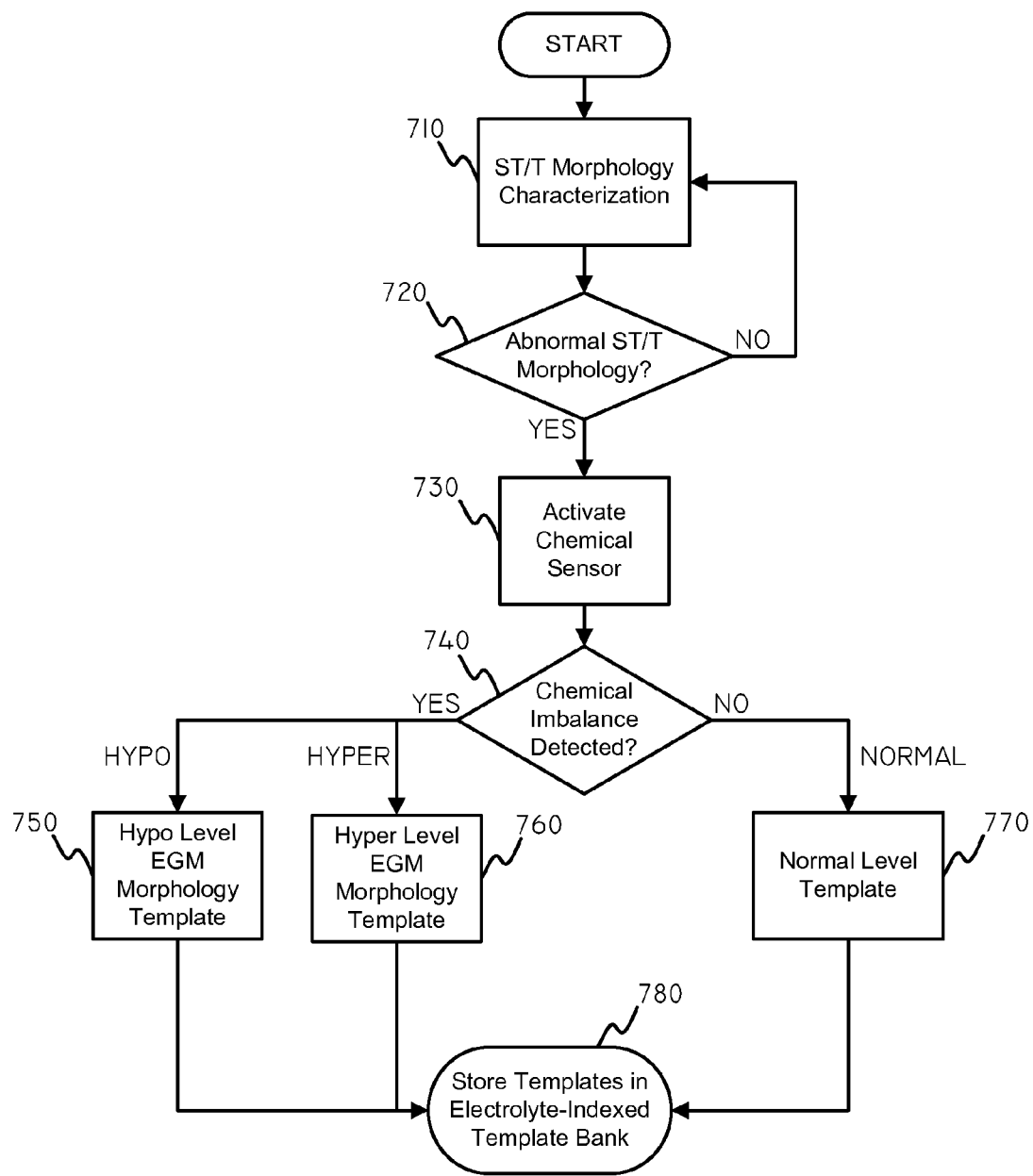
FIG. 7 is a flow chart in accordance with at least one embodiment of the invention.

It is believed that the changes to the EGM morphology caused by chemical concentration abnormalities exhibit a morphological signature that is repeatable within a given patient and within some patient populations. In some embodiments, such repeatable changes can be used to more quickly and accurately identify myocardial ischemia. One way to record and apply such repeatable changes is through the creation and/or application of morphology templates. FIG. 7 is a flow diagram in accordance with at least one embodiment of the invention illustrating the creation of morphology templates. In one operation, the ST/T morphology is characterized 710. In another operation, the system determines whether the ST/T morphology is abnormal 720. If the ST/T morphology is not abnormal, then the system can return to ST/T morphology characterization 710. However, if the ST/T morphology is abnormal, then a chemical sensor is activated 730. Data from the chemical sensor can be used to determine whether there is a chemical imbalance 740.

If data from the chemical sensor indicates that there is a chemical imbalance, then the EGM morphology can be recorded and used in conjunction with the chemical data in order to create an EGM morphology template. For example, if there is a chemical imbalance manifested as an abnormally low concentration of an electrolyte (hypo level), then a hypo-level electrogram (EGM) morphology template 750 can be created. If there is a chemical imbalance manifested as an abnormally high concentration of an electrolyte (hyper level), then a hyper-level electrogram (EGM) morphology template 760 can be created. If there are normal levels of chemical analytes, a normal level electrogram template 770 can be created.

Morphological templates created by the system can include the electrogram data points and/or the signal associated with the electrogram generated by an electrical sensor. The template can also include other data such as the particular chemical at issue, and the concentration of the chemical, or any other data that is relevant to the template. The morphological templates can be created by a processor. The processor can create such a template automatically or upon prompting from a system user.

The morphological templates (intending to refer to the hypo-level templates, the hyper-level templates, and the normal-level templates) can be stored in a chemical concentration-indexed template bank 780, in one embodiment. In one embodiment morphology templates are generated for abnormal physiological potassium concentrations, which can comprise measuring potassium concentrations and recording concurrent cardiac electrogram signals.

Figure 8:
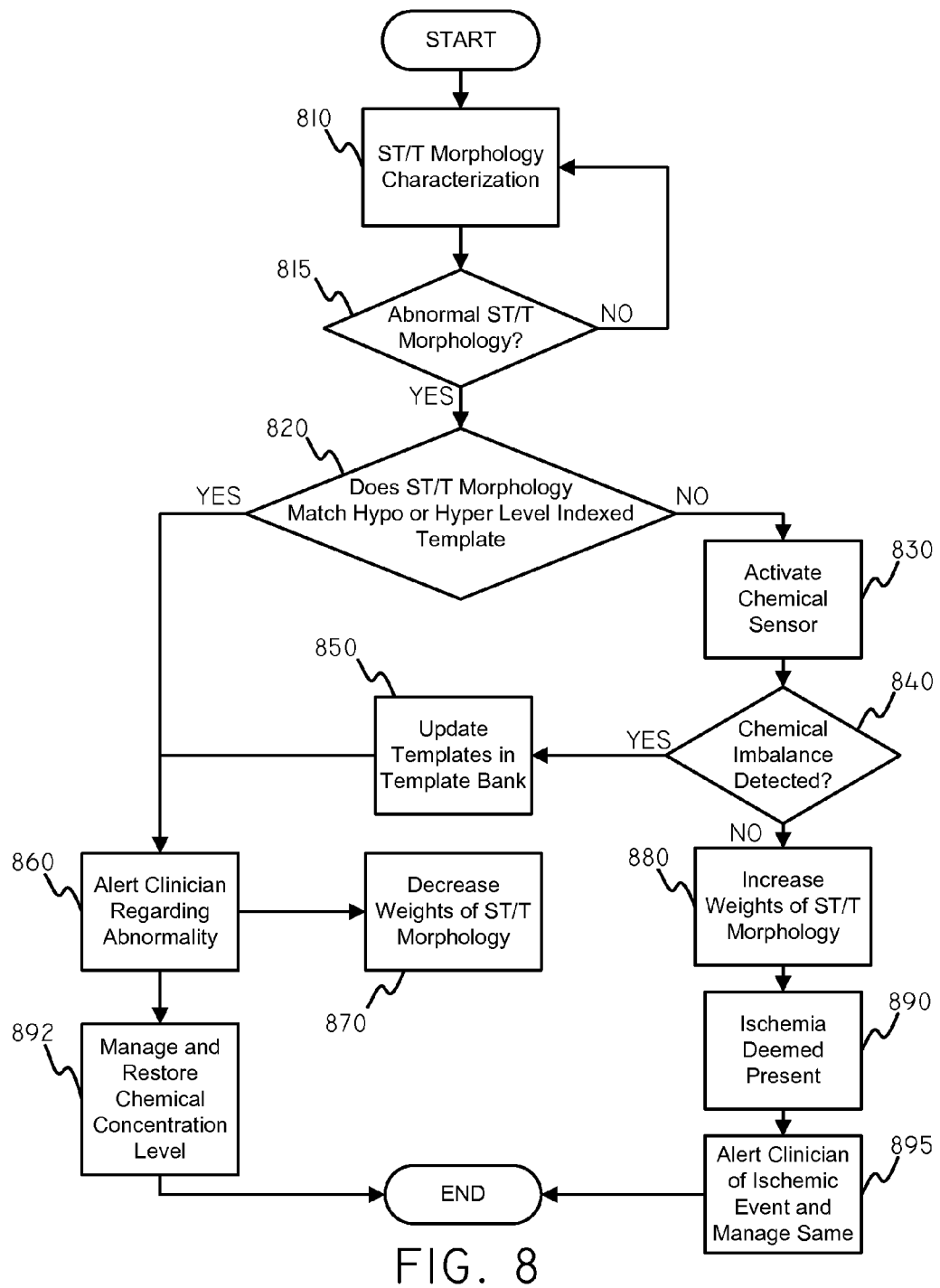
FIG. 8 is a flow chart in accordance with at least one embodiment of the invention.

After morphology templates are either derived by a system or programmed into a system, they can then be applied in order to identify myocardial ischemia more quickly and more accurately. FIG. 8 is a flow diagram in accordance with at least one embodiment of the invention illustrating a method of identifying myocardial ischemia using morphological templates. In a first operation, the ST/T morphology is characterized 810. In another operation, the system can determine whether or not the ST/T morphology is abnormal 815. In another operation, the ST/T morphology is compared to the ST/T morphological templates in a template bank 820. Specifically, it is determined whether measured ST/T morphology matches a hypo- or hyper-level indexed template. If there is a match, a clinician is alerted of a probable chemical abnormality 860. In some embodiments, the weight on the ST/T morphology for use in identifying ischemia is also decreased 870, at least temporarily. In some embodiments, therapy can be initiated in order to manage and restore chemical concentration levels 892.

However, if there is not a match, a chemical sensor is activated for confirmation 830. The activation of a chemical sensor can allow data to be generated that can help to determine whether or not myocardial ischemia is taking place, even if the ST/T morphology does not match one of the saved morphology templates.

The system can then analyze data from the chemical sensor to determine whether or not the patient has a chemical imbalance 840. If a chemical imbalance is not detected, the weight ST/T morphology analysis in ischemia detection algorithms is increased 880. However, if a chemical imbalance is detected, the morphology templates are acquired and updated in the template bank 850, and a clinician is alerted of the chemical abnormality 860. At that point therapy can be initiated so that the chemical concentrations can be managed and restored 892. In addition, the weights of ST/T morphology can be decreased 870.

If abnormal ST/T morphology is detected and if chemical concentrations are within normal bounds, then ischemia can be deemed to be present by the system 890. Optionally, other steps 895 can be performed including alerting a care provider of the ischemia and/or initiating appropriate management therapy for the ischemia.

It will be appreciated that the morphological templates that are applied in algorithms to detect myocardial ischemia can be dynamically generated by a given implanted medical device or can be programmed into an implanted medical device. As such, in some embodiments methods of the invention can even be applied in the context of devices that lack chemical sensors. For example, morphological templates that are appropriate for a population of patients can be determined empirically and then these templates can be programmed into devices. Then the devices can try to match observed ST/T morphologies with the stored templates. If observed ST/T morphology does not match a hypo- or hyper-chemical concentration template, then the device can deem myocardial ischemia to be present even without input from a chemical sensor.

In some embodiments, a difference vector can be calculated that represents the ST/T morphology deviations that are characteristic of hypokalemia and/or hyperkalemia. For example, ST/T morphology can be observed in patients wherein the potassium concentration is known (either because they have an implanted device with a chemical sensor or because potassium concentration is being assessed with an external device). In each individual patient, one or more difference vectors can then be calculated that represents the difference between the deviated ST/T morphology at a particular degree of hypo- or hyperkalemia and the normal ST/T morphology for that patient. In some embodiments, difference vectors can be calculated across a given patient population. Difference vectors can then be applied even in patients who have devices without chemical sensors. For example, the difference vectors can be loaded into a device without a chemical sensor and can then be added to a normal ST/T morphology for that patient in order to produce hypo- and/or hyper-chemical concentration morphological templates for that patient which can then be utilized as described above.

Figure 9:
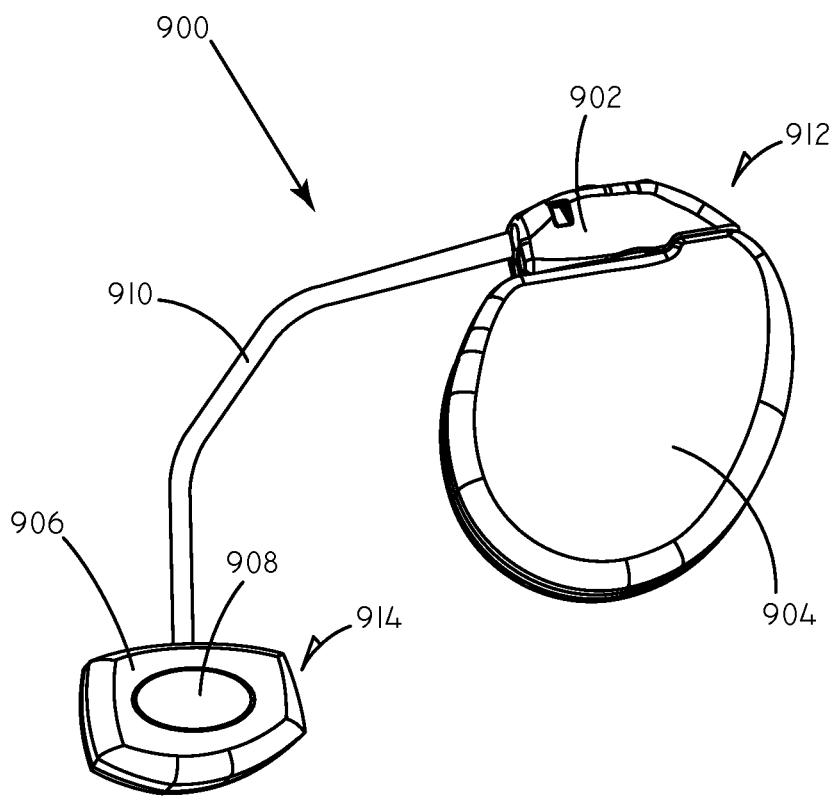
FIG. 9 is a schematic view of an implantable medical system in accordance with an embodiment of the invention.

It will be appreciated that in some embodiments a chemical sensor can be remote from a pulse generating device. Referring now to FIG. 9, a schematic view of an implantable medical system 900 is shown in accordance with another embodiment of the invention. A pulse generating device 912, including a housing 904 is coupled to a header 902. The pulse generating device 912 can be, for example, a pacemaker or an implantable cardioverter-defibrillator. The header 902 is coupled to a lead 910 which is, in turn, coupled to a sensor device 914. The sensor device 914 can include a housing 906 and a chemical sensor 908. The sensor device 914 and the pulse generating device 912 can be in signal communication. In some embodiments, lead 910 can be replaced with a wireless communication and power link.

Figure 10:
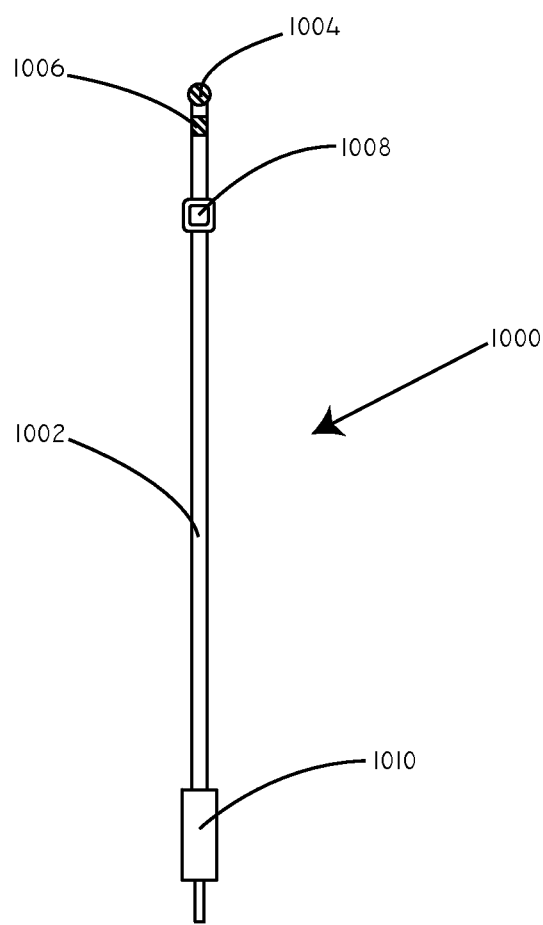
FIG. 10 is a schematic view of a stimulation lead in accordance with an embodiment.

In some embodiments, a chemical sensor can be integrated with a stimulation lead. By way of example, a chemical sensor can be integrated as part of a coronary sinus lead. Referring now to FIG. 10, a schematic diagram is shown of an exemplary stimulation lead 1000 ("lead") (not to scale) in accordance with an embodiment of the invention. The lead 1000 includes a lead body 1002, a distal pacing/sensing electrode 1004 (or tip electrode), a proximal pacing/sensing electrode 1006 (or ring electrode), a proximal end connector 1010, and a chemical sensor 1008. Though two pacing/sensing electrodes are shown in FIG. 10, it will be appreciated that lead 1000 can include as few as one pacing/sensing electrode or as many as ten or more. The proximal end connection 1010 can be configured to fit within a port in a header of a CRM device. By way of example, the proximal end can structurally conform to a standard for lead-header interfaces such as the IS-1, IS-4, or DF-1 standards. The electrodes can include metals such as noble metals. Specifically, the electrodes can include platinum. In some cases, the electrodes can include alloys such as an alloy of platinum and iridium. In some embodiments, the lead 1000 can also include shocking coils (not shown). The lead 1000 can include conductors (not shown), such as optical and/or electrical conductors, within the lead body 1002. The conductors can provide optical and/or electrical communication between the proximal end connector 1010 and the electrodes and/or the chemical sensor.

In some embodiments, a chemical sensor disposed on a lead disposed within the coronary venous system of a patient can be configured to measured oxygen saturation levels. As such, in some embodiments, oxygen saturation levels within the coronary venous system can be used in conjunction with S-T segment deviation in order to detect myocardial ischemia. For example, where oxygen saturation levels are found to be low, the probability that an ischemic event is occurring is higher. As such, in any of the methods described herein, a step of evaluating oxygen saturation within the coronary venous system can be optionally included.

In some embodiments, metabolic workload estimation can be used in conjunction with S-T segment deviation and chemical analyte concentration data in order to detect myocardial ischemia. It is believed that metabolic workload can influence S-T segment deviation and therefore including metabolic workload in a method of detecting myocardial ischemia is believed to lead to increased accuracy of detection. Metabolic workload can be estimated in various ways. By way of example, metabolic workload can be estimated based on accelerometer data and/or on minute ventilation data.

As such, in a particular embodiment, the system can be configured to evaluate metabolic workload when determining whether or not ST/T morphology is abnormal. For example, in the context of the method depicted in FIG. 8, the system can determine whether or not ST/T morphology is abnormal 820 based as a function of metabolic workload in some embodiments. Thus, what would qualify as abnormal ST/T morphology can depend on the estimated metabolic workload. One technique for implementing such an approach is that ST/T templates in a template bank can be indexed based on estimated metabolic workload. A given ST/T template may correspond to a particular range of estimated metabolic workload while other ST/T templates may correspond to different particular ranges of estimated metabolic workload.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable medical device comprising:
   control circuitry;
   an electrical field sensor in communication with the control circuitry, the electrical field sensor configured to generate a signal corresponding to cardiac electrical fields;
   a chemical sensor in communication with the control circuitry, the chemical sensor configured to generate a signal corresponding to the concentration of a physiological analyte that affects cardiac electrical field waveform morphology; and
   a template bank;
   the control circuitry configured to monitor for the presence of myocardial ischemia by evaluating both the signal generated by the electrical field sensor and the signal generated by the chemical sensor; the control circuitry configured to generate a cardiac electrical field morphological template including data from the signal corresponding to cardiac electrical fields and chemical concentration data from the signal corresponding to the concentration of potassium and store the cardiac electrical field morphological template in the template bank; wherein the control circuitry stores the cardiac electrical field template as a hypo-level template if the potassium concentration is abnormally high, a normal level template if the potassium concentration is normal, and a hyper-level template if the potassium concentration is abnormally high.

2. The implantable medical device of claim 1, the electrical field sensor comprising a first electrode and a second electrode.

3. The implantable medical device of claim 1, the chemical sensor comprising an optical chemical sensor.

4. The implantable medical device of claim 3, the optical chemical sensor comprising a light source, a light detector, and a chemical sensing element.

5. The implantable medical device of claim 1, the control circuitry configured to identify episodes of myocardial ischemia with the signal generated by the electrical field sensor and confirm the accuracy of such identification with the signal generated by the chemical sensor.

6. The implantable medical device of claim 5, wherein episodes of myocardial ischemia are identified based on ST-segment deviation.

7. The implantable medical device of claim 5, wherein episodes of myocardial ischemia are confirmed based on a concentration of potassium between about 3.8 meq and about 5.0 meq.

8. The implantable medical device of claim 1, the control circuitry further configured to generate an alert when myocardial ischemia is present based on evaluating both the signal generated by the electrical field sensor and the signal generated by the chemical sensor.

9. The implantable medical device of claim 1, wherein the chemical sensor is chronically implantable.

10. The implantable medical device of claim 1, the control circuitry configured to initiate therapy to alleviate chemical imbalance.

11. The implantable medical device of claim 1, the control circuitry configured to adjust a ST/T morphology weighting parameter to make it less likely that an observed ST/T morphology as derived from the signal corresponding to cardiac electrical fields is deemed abnormal if a chemical imbalance is detected.

12. The implantable medical device of claim 1, the control circuitry configured to selectively activate the chemical sensor based on the signal generated by the electrical field sensor.

13. The implanted medical device of claim 1, the signal corresponding to cardiac electrical fields comprising an ST/T morphology, the control circuitry configured to compare the ST/T morphology with a previously stored hypo-level template or hyper-level template.

14. The implanted medical device of claim 13, the device configured to send an alert regarding a probable chemical abnormality if the ST/T morphology matches with the previously stored hypo-level template or the hyper-level template.

* * * * *